US007585651B2

(12) United States Patent
Akimoto et al.

(10) Patent No.: US 7,585,651 B2
(45) Date of Patent: Sep. 8, 2009

(54) PROCESS FOR PRODUCING ARACHIDONIC ACID-CONTAINING LIPIDS

(75) Inventors: Kengo Akimoto, Mishima-gun (JP); Kenichi Higashiyama, Mishima-gun (JP); Sakayu Shimizu, Kyoto (JP)

(73) Assignee: Suntory Holdings Limited, Osaki-shi, Osaka (JP)

( * ) Notice: Subject to any disclaimer, the term of this patent is extended or adjusted under 35 U.S.C. 154(b) by 200 days.

(21) Appl. No.: 11/167,224

(22) Filed: Jun. 28, 2005

(65) Prior Publication Data

US 2005/0266538 A1 Dec. 1, 2005

Related U.S. Application Data

(62) Division of application No. 09/530,260, filed as application No. PCT/JP99/04653 on Aug. 27, 1999, now abandoned.

(30) Foreign Application Priority Data

Aug. 28, 1998 (JP) ................................ 10-243583

(51) Int. Cl.
C12P 7/64 (2006.01)
(52) U.S. Cl. ........................ 435/134; 435/136; 435/911
(58) Field of Classification Search ....................... None
See application file for complete search history.

(56) References Cited

U.S. PATENT DOCUMENTS

| 4,916,066 A | 4/1990 | Akimoto et al. ............. 435/134 |
| 5,093,249 A | 3/1992 | Nakajima et al. ........... 435/135 |
| 5,204,250 A | 4/1993 | Shinmen et al. ............. 435/134 |
| 5,583,019 A | 12/1996 | Barclay ....................... 435/134 |
| 5,658,767 A | 8/1997 | Kyle |

FOREIGN PATENT DOCUMENTS

| EP | 0 535 940 A1 | 4/1993 |
| JP | 1-243992 | 9/1989 |
| JP | 2-142486 | 5/1990 |
| JP | 3-49688 | 3/1991 |
| JP | 3-72892 | 3/1991 |
| JP | 5-91887 | 4/1993 |
| JP | 06-172263 | 6/1994 |
| JP | 7-34752 | 4/1995 |
| JP | 8-214893 | 8/1996 |
| WO | 96/21037 | 7/1996 |
| WO | 98/39468 | 9/1998 |

OTHER PUBLICATIONS

Shimizu, S. (Oils-Fats-Lipids 1995, Proceedings of the World Congress of the International Society for Fat Research, 21st, The Hague, Oct. 1-6, 1995, vol. 1, 103-109).*
Carlson et al., "The Effect of Marine Oil-Supplemented Formulas with and without Eicosapentaenoic Acid on the N-3 and N-6 Fatty Acid Status and Growth of Premature Infants," Advances In Polyunsaturated Fatty Acid Research, 1993, pp. 261-264.
Carlson et al., "Arachidonic Acid Status Correlates with First Year Growth in Preterm Infants," Proc. Natl. Acad. Sci. USA, vol. 90, Feb. 1993, pp. 1073-1077.
Lanting et al., "Neurological Differences Between 9-Year-Old Children Fed Breast-Milk or Formula-Milk as Babies," The Lancet, vol. 344, Nov. 1994, pp. 1319-1322.
Shinmen et al., "Production of Arachindonic Acid by Mortieralla Fungi: Selection of a Potent Producer and Optimization of Culture Conditions for Large-Scale Production," Applied Microbiology and Biotechnology, vol. 31, 11-16, 1989, pp. 56-61.
Totani et al., "Industrial Production of Arachidonic Acid by Mortieralla," Industrial Applications of Single Cell Oils, Chpt. 4, 1992, pp. 52-60.
Shimizu et al., "Production of Eicosapentaenoic Acid by Mortieralla Fungi," Journal of the American Oil Chemists' Society, vol. 65, No. 9, Sep. 1988, pp. 14-18.
Shimizu et al., "Fungal Mycelia as a Novel Source of Eicosapentaenoic Acid: Activation of Enzyme(s) Involved in Eicosapentaenoic Acid Product at Low Temperature," Biochemical and Biophysical Research Communications, vol. 150, No. 1, Jan. 1988, pp. 335-341.
Lindberg et al., "Effect of Temperature and Glucose Supply on the Production of Polyunsaturated Fatty Acids by the Fungus Mortieralla alpina CBS 343.66 in Fermentor Cultures," Applied Microbiology and Biotechnology, vol. 39, 1993, pp. 450-455.
Shimada et al., "Enrichment of Arachidonic Acid: Selective Hydrolysis of a Single-Cell Oil From Mortieralla with Candida Cylindraces Lipase," Journal of the American Oil Chemists' Society, vol. 72, No. 11, 1995, pp. 1323-1327.
Li et al., "Process for Production of Arachidonic Acid Concentrate by a Strain of Mortieralla alpina," The Canadian Journal of Chemical Engineering, vol. 73, Feb. 1995, pp. 135-139.
Shimada et al., "Enzymatic Enrichment of Arachidonic Acid From Mortieralla Single-Cell Oil," Journal of the American Oil Chemists' Society, vol. 75, No. 9, 1998, pp. 1213-1217.
Shimizu et al., "Production of useful fatty acids by microbial processes", Recent Res. Devel. In Lipids Res., vol. 1, 1997, pp. 267-286, XP001026965.

(Continued)

Primary Examiner—Irene Marx
(74) Attorney, Agent, or Firm—Drinker Biddle & Reath LLP

(57) ABSTRACT

A process for producing lipids containing arachidonic acid comprising culturing a microorganism in which ω3 desaturase activity has been decreased or is lacking at a temperature lower than the optimum growth temperature from the start of culturing or after culturing at the optimum growth temperature, said microorganism being obtained by the mutation treatment of a microorganism capable of producing arachidonic acid and belonging to the genus *Mortierella* and the like; and then recovering lipids containing arachidonic acid from the culture.

4 Claims, No Drawings

OTHER PUBLICATIONS

Spychalla et al., "*Identification of an animal ω03 fatty acid desaturase by heterologous expression in Arabidopsis*", Proceedings of the National Academy of Sciences of USA, vol. 94, pp. 1142-1147, Feb. 1997, XP-002076628.

Nagao et al., In Industrial Applications of Single Cell Oils, Kyle et al., eds., Amer. Oil Chemists' Soc'y, Champaign, IL, pp. 52-60 (1992).

Jareonkitmongkol et al., "Isolation and characterization of an ω3-desaturase-defective mutant of an arachidonic acid-producing fungus, *Mortierella alpina* IS-4," *Arch. Microbiol.* 161: 316-19 (1994).

Office Action issued by European Patent Office in the copending European Application No. 99 940 538.4, May 7, 2009.

Totani et al., "The filamentous fungus *Mortierella alpina*, high in arachidonic acid," *Lipids* 22(12): 1060-62 (1987).

Singh et al., "Production of high yields of arachidonic acid in a fed-batch system by *Mortierella alpina* ATCC 32222," *Appl. Microbiol. Biotech.* 48: 1-5 (1997).

Bajpai et al., "Production of arachidonic acid by *Mortierella alpina* ATCC 32222," *J. Indus. Microbiol.* 8: 179-86 (1991).

* cited by examiner

PROCESS FOR PRODUCING ARACHIDONIC ACID-CONTAINING LIPIDS

This application is a divisional of application Ser. No. 09/530,260, filed on Jul. 12, 2000, which is a national stage filing under 35 U.S.C. 371 of International Application No. PCT/JP99/04653, filed on Aug. 27, 1999.

FIELD OF THE INVENTION

The present invention relates to a process for producing lipids containing arachidonic acid or a process for producing lipids containing dihomo-γ-linolenic acid by fermentation using a mutant in which ω3 unsaturation activity is decreased or deleted.

BACKGROUND ART

There are reports that arachidonic acid, as is docosahexaenoic acid, contained in breast milk and plays a role in the infant's development ("Advances in Polyunsaturated Fatty Acid Research," Elsevier Science Publishers, 1993, pp. 261-264) and reports on the importance of arachidonic acid in the development of fetus's height and brain (Proc. Natl. Acad. Sci. U.S.A., 90, 1073-1077 (1993), Lancet, 344, 1319-1322 (1994)), and accordingly there are moves to supplement infant formula with arachidonic acid and docosahexaenoic acid that represent major differences in the fatty acid composition between breast milk and infant formula.

The FAO/WHO has issued a recommendation that the intake of arachidonic acid and docosahexaenoic acid be 60 mg/kg/day and 40 mg/kg/day, respectively, for permature infants and the intake of arachidonic acid and docosahexaenoic acid be 40 mg/kg/day and 20 mg/kg/day, respectively, for mature infants.

As methods of obtaining these fatty acids in large amount, there are conventionally known production methods that utilize microorganisms. For example, a method utilizing a microorganism belonging to the genus *Mortierella* has been proposed that permits the production of arachidonic acid in a shorter culturing time, with a higher yield, and using simpler processes using an inexpensive commonly used medium (Japanese Examined Patent Publication (Kokoku) No. 7-34752).

However, the percentage of arachidonic acid in the total fatty acids is not satisfactory with these conventional production methods. Thus, when lipids containing arachidonic acid are to be added to foods, the highest possible content of arachidonic acid is preferred since it can minimize the amount of undesirable substances added and therefore it is also desirable in terms of quality and cost. It is also desirable when arachidonic acid ethyl esters are to be isolated and purified, since the highest possible content of arachidonic acid providing highly purified products with simple procedures and at low cost.

As methods of enhancing the percentage of arachidonic acid in lipids relative to the total fatty acids, there are many methods known in the art. For example, by culturing *Mortierella alpina* at 28° C. in a normally airation and agitation culture followed by culturing for further 6 days under the condition of complete glucose depletion, the percentage of arachidonic acid has successfully been raised to 67.4% (Appl. Microbial. Biotechnol. 31, 11-6 (1989)). This method, however, takes advantage of the fact that microorganisms in a starved state effect β-oxidation of fatty acids of triglyceride with a low degree of saturation to convert them to energy. Therefore, there are actually no changes in the total amount of arachidonic acid, and due to the reduction of fatty acids with a low degree of saturation only the relative percentage of arachidonic acid is enhanced. Thus, it does not mean that the amount of produced triglycerides containing a high percentage of arachidonic acid is increased, but on the contrary it appears that the percentage of triglycerides is also decreased as a result of β-oxidation.

It is known that at a temperature lower than the optimum growth temperature, microorganisms capable of producing arachidonic acid generally try to adapt to low-temperature environments by enhancing the degree of unsaturation of unsaturated fatty acids so as to maintain fluidity and the functions of the cell membrane, and thereby the activity of Δ6 desaturase and Δ5 desaturase become enhanced so that fatty acids having a high degree of unsaturation such as arachidonic acid are produced in greater amounts. Culturing at a low temperature is therefore desirable to enhance the content of arachidonic acid.

In a method utilizing the above property, *Mortierella alpina* was cultured in an airation and agitation culture at 20° C. for 16 days in which the percentage of arachidonic acid was successfully enhanced to 71.2% ("Industrial Applications of Single Cell Oils," American Oil Chemists' Society Champaign, 1992, pp. 52-60). It is known, however, that since this method requires a long time for culturing, it is not only unsuitable for industrial production but at the low temperature a part of arachidonic acid that was produced is converted to eicosapentaenoic acid by a ω3 desaturase (Biochem. Biophys. Res. Commun., 150, 335-341 (1988)) that acts at low temperatures thereby reducing the percentage of arachidonic acid and increasing the percentage of eicosapentaenoic acid in the total fatty acids.

For example, when filamentous fungus of the genus *Mortierella* is cultured at 12° C. for 7 weeks, ω3 desaturase is activated and the percentage of EPA to the total fatty acids reaches 2 to 20% (J. Am. Oil Chem. Soc., 65, 1455-1459 (1988)) and accordingly the percentage of arachidonic acid decreases. In contrast, by using strains wherein ω3 desaturase is decreased or is lacking, the percentage of arachidonic acid to the total fatty acids in the lipid can be enhanced to 50% or more, and when mutation is repeated it can be enhanced to 70% or more and the percentage of EPA can be kept at 0.5% or less.

Little eicosapentaenoic acid is contained in breast milk, and recent studies have even shown that it is detrimental to the development of babies of premature infants ("Advances in Polyunsaturated Fatty Acid Research," Elsevier Science Publishers, 1993, pp. 261-264). Thus, there is a strong need for the development of a method that can produce lipids containing a high percentage of arachidonic acid and containing little or no eicosapentaenoic acid using an inexpensive commonly used medium, a simple process, and on a large scale.

On the other hand, dihomo-γ-linolenic acid is converted to arachidonic acid by a Δ5 desaturase irrespective of the culture temperature. As a method of producing dihomo-γ-linolenic acid on a large scale by a fermentation at low cost, there is a known method of culturing by adding a substance that inhibits the activity of Δ5 desaturase such as sesamin, episesamin, sesaminol, episesaminol, and curcumin to the medium, or a method of culturing using a mutant strain of a microorganism capable of producing arachidonic acid in which mutation has been induced so that Δ5 desaturase activity is decreased or deleted (Japanese Unexamined Patent Publication (Kokai) No. 1-243992, Japanese Unexamined Patent Publication (Kokai) No. 3-72892, Japanese Unexamined Patent Publication (Kokai) No. 3-49688, and Japanese Unexamined Patent Publication (Kokai) No. 5-91887).

In this case also, however, culturing at a temperature lower than the optimum growth temperature such as 12° C. in an attempt to enhance the dihomo-γ-linolenic acid content would result in the activation of the above-mentioned ω3 desaturase so that concern arises that a part of dihomo-γ-linolenic acid may be converted to 8, 11, 14, 17-eicosatetraenoic acid and thereby the percentage of dihomo-γ-linolenic acid may decrease and that of 8, 11, 14, 17-eicosatetraenoic acid may increase. Thus, there is a strong need for the development of a method that can produce lipids containing a high percentage of dihomo-γ-linolenic acid using an inexpensive commonly used medium, a simple process, and on a large scale.

DISCLOSURE OF THE INVENTION

Thus, the present invention is intended to provide a process for producing arachidonic acid-containing lipids containing a high percentage of arachidonic acid and containing little or no eicosapentaenoic acid using an inexpensive conventionally-used medium, a simple process, and on a large scale, and a process for producing lipids containing a high percentage of dihomo-γ-linolenic acid and containing little or no eicosapentaenoic acid or 8, 11, 14, 17-eicosatetraenoic acid using an inexpensive conventionally-used medium, a simple process, and on a large scale.

After extensive research in order to attain the above objectives, the inventors of the present invention have found a microorganism in which ω3 desaturase activity is decreased or deleted and which is obtained by the mutagenesis of a microorganism capable of producing arachidonic acid, and thereby have completed the present invention.

Thus, the present invention is intended to provide a process for producing lipids containing arachidonic acid comprising the steps of culturing a microorganism wherein ω3 desaturase activity has been decreased or is lacking at a temperature lower than the optimum growth temperature from the start of culturing or after culturing at the optimum growth temperature, said microorganism being obtained by the mutagenesis of a microorganism capable of producing arachidonic acid and belonging to the genus *Mortierella*, the genus *Conidiobolus*, the genus *Pythium*, the genus *Phytophthora*, the genus *Penicillium*, the genus *Cladosporium*, the genus *Mucor*, the genus *Fusarium*, the genus *Aspergillus*, the genus *Rhodotorula*, the genus *Entomophthora*, the genus *Echinosporangium* or the genus *Saprolegnia*; and then recovering lipids containing arachidonic acid from the culture.

Furthermore, the present invention is intended to provide a process for producing lipids containing arachidonic acid comprising the steps of culturing a microorganism wherein ω3 desaturase activity has been decreased or is lacking at a temperature lower than 20° C. from the start of culturing or after culturing at 20 to 40° C., said, microorganism being obtained by the mutagenesis of a microorganism belonging to the subgenus *Mortierella*; and then recovering lipids containing arachidonic acid from the culture.

The present invention is also intended to provide a process for producing lipids containing dihomo-γ-linolenic acid comprising the steps of culturing a microorganism wherein ω3 desaturase activity has been decreased or is lacking at a temperature lower than the optimum growth temperature from the start of culturing or after culturing at the optimum growth temperature, said microorganism being obtained by the mutagenesis of a microorganism that is capable of producing arachidonic acid in which microorganism Δ5 desaturase activity has been decreased or is lacking, and that belongs to the genus *Mortierella*, the genus *Conidiobolus*, the genus *Pythium*, the genus *Phytophthora*, the genus *Penicillium*, the genus *Cladosporium*, the genus *Mucor*, the genus *Fusarium*, the genus *Aspergillus*, the genus *Rhodotorula*, the genus *Entomophthora*, the genus *Echinosporangium* or the genus *Saprolegnia*; and then recovering lipids containing dihomo-γ-linolenic acid from the culture.

Furthermore, the present invention is intended to provide a process for producing lipids containing dihomo-γ-linolenic acid comprising the steps of culturing a microorganism wherein ω3 desaturase activity has been decreased or is lacking at a temperature lower than 20° C. from the start of culturing or after culturing at 20 to 40° C., said microorganism being obtained by the mutagenesis of a microorganism in which Δ5 desaturase activity has decreased or is lacking, which had been obtained by the mutagenesis of a microorganism belonging to subgenus *Mortierella*; and then recovering lipids containing dihomo-γ-linolenic acid from the culture.

EMBODIMENT FOR CARRYING OUT THE INVENTION

In accordance with the present invention, as microorganisms that are subjected to mutagenesis, there can be mentioned microorganisms belonging to the genus *Mortierella*, the genus *Conidiobolus*, the genus *Pythium*, the genus *Phytophthora*, the genus *Penicillium*, the genus *Cladosporium*, the genus *Mucor*, the genus *Fusarium*, the genus *Aspergillus*, the genus *Rhodotorula*, the genus *Entomophthora*, the genus *Echinosporangium* and the genus *Saprolegnia*, and more preferably microorganisms belonging to the genus *Mortierella*, the genus *Conidiobolus*, the genus *Pythium*, the genus *Entomophthora*, the genus *Echinosporangium* and the genus *Saprolegnia* that have Δ6 desaturase and Δ5 desaturase and that can produce fatty acids up to arachidonic acid in the fatty acid biosynthetic pathway.

More specifically, there can be mentioned *Pythium insidiosm* ATCC28251 as a microorganism belonging to the genus *Pythium*; *Echinosporangium transversalis* ATCC16960 (NRRL3116) and ATCC18036 (NRRL5525) as a microorganism belonging to the genus *Echinosporangium*; *Saprolegnia ferax* CBS534.67, *Saprolegnia lapponica* CBS284.38, *Saprolegnia litoralis* CBS535.67, *Saprolegnia moniligera* CBS558.67, and *Saprolegnia turfosa* CBS313.82 and the like as a microorganism belonging to the genus *Saprolegnia*.

Specifically, in accordance with the present invention, microorganisms belonging to the genus *Mortierella* subgenus *Mortierella* that have a high ability of producing arachidonic acid are preferred. As microorganism belonging to the genus *Mortierella* subgenus *Mortierella* of the present invention, there can be mentioned *Mortierella elongata*, *Mortierella exigua*, *Mortierella hygrophila*, *Mortierella alpina*, *Mortierella parvispora*, *Mortierella beljakovae*, *Mortierella globalpina*, *Mortierella epigama*, *Mortierella kuhlmanii*, *Mortierella acrotona*, *Mortierella zychae*, *Mortierella rishikesha*, *Mortierella minutissima*, *Mortierella bainieri*, *Mortierella schmuckeri*, and the like, and specifically there can be mentioned strains *Mortierella elongata* IFO8570, *Mortierella exigua* IFO8571, *Mortierella hygrophila* IFO5941, *Mortierella alpina* IFO8568, ATCC16266, ATCC32221, ATCC42430, CBS219.35, CBS224.37, CBS250.53, CBS343.66, CBS527.72, CBS529.72, CBS608.70, and CBS754.68, and the like.

These strains are all available without limitations from the Institute for Fermentation Osaka (IFO), Japan, and American Type Culture Collection (ATCC) in the U.S.A., and Centrralbureau voor Schimmelcultures (CBS). It is also possible to use *Mortierella elongata* SAM0219 (FERM P-8703) (FERM BP-1239) that is a microbial strain our research group has isolated from the soil.

In accordance with the present invention, microorganisms that are subjected to mutagenesis are not limited to those wild type strains described above but preferably include mutants or recombinants of the above microorganisms (wild type strains) belonging to the genus *Mortierella* subgenus *Mortierella*, in other words those that have been deliberately designed to have a higher content of arachidonic acid or dihomo-γ-linolenic acid in lipids, or a higher content of total lipid than those produced by the original wild type strains, when they are cultured in the presence of the same substrate.

Further included are those microorganisms that were designed to produce unsaturated fatty acids at an amount equal to that produced by the wild type strains by efficiently using substrates having excellent cost effectiveness. For example, as a mutant strain in which Δ12 desaturase activity is lacking and Δ6 desaturase activity has been enhanced, there can be mentioned *Mortierella alpina* SAM2086 (FERM BP-6032), and as a mutant strain lacking Δ5 desaturase activity that was artificially induced to enhance the productivity of dihomo-γ-linolenic acid, there can be mentioned *Mortierella alpina* SAM1860 (FERM BP-3589).

In accordance with the present invention, by subjecting mutant strains of the present invention in which ω3 desaturase has been decreased to mutagenesis, it is also possible to obtain mutant strains in which ω3 desaturase activity has been further decreased or is lacking.

ω3 desaturase activity as used herein refers to an action of inserting a double bond in between the third and the fourth carbons from the methyl group of a fatty acid, and microorganisms in which ω3 desaturase activity has been decreased or is lacking can be easily evaluated for the decrease or lack of ω3 desaturase activity thereof.

Specifically, for the production of lipids containing arachidonic acid, it can be evaluated by the percentage of eicosapentaenoic acid in the total fatty acids in the microbial cells after a mutant that was obtained by the mutagenesis of the parent strain is cultured at a temperature lower than the optimum growth temperature, for example a temperature lower than 20° C. Thus, when the percentages of eicosapentaenoic acid in the parent strain and the mutant strain under culturing at a low temperature are compared and the percentage of eicosapentaenoic acid of the parent strain is set at 1, then if the percentage of the mutant strain is lower than 1, the activity is judged to be decreased, while if it is 0, the activity is judged to be lacking.

For the production of lipids containing dihomo-γ-linolenic acid also, it can be evaluated by the percentage of 8, 11, 14, 17-eicosatetraenoic acid in the total fatty acids in the microbial cells after a mutant that was obtained by the mutagenesis of the parent strain (for example, a parent strain in which Δ5 desaturase activity has been decreased or lacked) was cultured at a temperature lower than the optimum growth temperature, for example a temperature lower than 20° C. Thus, when the percentages of 8, 11, 14, 17-eicosatetraenoic acid in the parent strain and the mutant strain under culturing at a low temperature are compared and the percentage of 8, 11, 14, 17-eicosatetraenoic acid of the parent strain is set at 1, then if the percentage of the mutant strain is lower than 1, the activity is judged to be decreased, while if it is 0, the activity is judged to be lacking.

As microorganisms for use in the process of producing dihomo-γ-linolenic acid of the present invention, mutant strains in which ω3 desaturase activity has been decreased or is lacking, that are obtained by the mutagenesis of microorganisms capable of producing arachidonic acid can be used, and more preferably mutant strains in which further Δ5 desaturase activity has been decreased or is lacking, are used. In order to obtain mutant strains in which ω3 desaturase activity has been decreased or is lacking and Δ5 desaturase activity also has been decreased or is lacking, a mutant strain obtained according to the present invention in which ω3 desaturase activity has been decreased or lacked is further subjected to mutagenesis and thereby mutant strains in which Δ5 desaturase activity has also been decreased or lacked are selected. Alternatively, they are also obtained by subjecting strains in which Δ5 desaturase activity has been already decreased or is lacking to mutagenesis so as to decrease or delete ω3 desaturase activity.

Mutation treatment according to the present invention can be conducted by conventional mutagenesis: for example effecting irradiation treatment (X ray, gamma ray, neutron beams, heavy ions), ultra violet irradiation, high temperature treatment and the like to induce mutation; and by suspending microorganisms in a suitable buffer, to which a mutagen is added followed by incubating for a given time, which is diluted appropriately and inoculated on an agar medium to obtain colonies of mutant strains.

As mutagens, alkylating agents such as nitrogen mustard, methyl methane sulfonate (MMS), and N-methyl-N-nitro-N-nitrosoguanidine (NTG), base analogs such as 5-bromouracil, antibiotics such as mitomycin C, base synthetic inhibitors such as 6-mercaptopurine, dyes such as proflavine (other derivatives), certain carcinogens such as 4-nitroquinoline-N-oxide, and other compounds such as manganese chloride and formaldehyde, and the like may be mentioned. Microorganisms used may be live cells (mycelia etc.) or spores.

As mutant strains of the present invention, for example, *Mortierella alpina* SAM2153 (Accession No. FERM P-15767) (Accession No. FERM BP-6794) wherein ω3 desaturase activity has been extremely decreased that was induced by the present inventors from *Mortierella alpina* IFO8568 capable of producing arachidonic acid can be used, but it is not limiting said to strain, and all other mutant strains that exhibit the ratio of an activity of smaller than 1 relative to eicosapentaenoic acid of the parent strain cultured under a low-temperature condition set as 1. The mutant strain, *Mortierella alpina* SAM2153, was deposited as a national deposition in Japan on Aug. 5, 1996 and was given the deposit Accession No. FERM P-i 5767. On Jul. 26, 1999, the International Depository Authority accented a request for transfer to a deposit under the Budapest Treaty and was thus given the deposit Accession No. BP-6794. The International Depository Authority is National Institute of Science and Human-Technology Agency of Industrial Science and Technology which is located at 1-3. Higashi 1 chome. Tsukuba-shi. Ibaraki-ken. 305-8566. Japan.

In order to culture the microbial strains for use in the present invention, spores, mycelia, or a preculture that has been previously cultured are inoculated to liquid media or solid media and are cultured. In the case of liquid media, carbon sources include, but not limited to, any of glucose, fructose, xylose, saccharose, maltose, soluble starch, molasses, glycerol, mannitol and the like that are commonly used. As nitrogen sources, in addition to natural nitrogen sources such as peptone, yeast extract, malt extract, meat extract, casamino acid, corn steep liquor, soy flour, defatted soybean meal and cottonseed meal, defined organic nitrogen sources such as urea and inorganic nitrogen sources such as sodium nitrate, ammonium nitrate, and ammonium sulfate can be used. For large scale industrial production of fatty acids or lipids containing them, liquid media are preferably used.

When desired, inorganic salts such as phosphates, magnesium sulfate, iron sulfate, and copper sulfate, and vitamins can also be used as trace nutrients. The concentrations of these medium components are not limited as long as they do not adversely affect microbial growth. Generally, from a practical viewpoint, carbon sources are in the range of 0.1 to 40% by weight and preferably 1 to 25% by weight, nitrogen sources are in the range of 0.01 to 10% by weight and preferably 0.1 to 10% by weight, and more preferably the initial amount added of carbon sources is 1 to 5% by weight, and that of nitrogen sources is 0.1 to 6% by weight and, during culturing, carbon sources and nitrogen sources, and more preferably only carbon sources, are fed.

The mutant strains of the present invention may be cultured at a temperature lower than the optimum growth temperature from the start of the culturing, or after culturing at the optimum growth temperature they may be cultured at a temperature lower than the optimum growth temperature. Though the optimum growth temperature as used herein may vary depending on the microorganism used, it is preferably 20 to 40° C. and preferably 20 to 30° C., and a temperature lower than the optimum growth temperature is a temperature lower than 25° C., preferably a temperature lower than 20° C., and more preferably a temperature lower than 20° C. and higher than 5° C. By means of the temperature control described above, the accumulation of lipids in the cells can be enhanced.

When culturing is effected at a temperature lower than the optimum growth temperature, culturing is conducted for 2 to 20 days, preferably 2 to 14 days. When culturing is conducted at the optimum growth temperature prior to culturing at a temperature lower than the optimum growth temperature, culturing is conducted for 1 to 6 days and preferably 1 to 4 days at the optimum growth temperature, and 2 to 14 days and preferably 2 to 10 days at a temperature lower than the optimum growth temperature.

pH of the medium is 4 to 10 and preferably 6 to 9, and airation and agitation culture, shaking culture, or stationary culture is conducted.

When cultured in a solid culture, bran, chaff, rice bran or the like to which 50 to 100% by weight of water relative to the weight of the solid has been added is used, and cultured at the above temperature for 3 to 14 days. In this case, nitrogen sources, inorganic salts, and trace nutrients may be added as desired.

Furthermore, in accordance with the present invention, a substrate for biosynthesis for arachidonic acid or dihomo-γ-linolenic acid may be added to a medium to facilitate the accumulation of arachidonic acid or dihomo-γ-linolenic acid. Examples of substrates for biosynthesis include hydrocarbons such as tetradecane, hexadecane, and octadecane, fatty acids such as tetradecanoic acid, hexadecanoic acid, and octadecanoic acid or salts (e.g. sodium salts and potassium salts) or esters thereof, or lipids containing fatty acids as components (e.g. olive oil, coconut oil, and palm oil).

Arachidonic acid or dihomo-γ-linolenic acid can be more effectively accumulated by culturing with the addition of said omega 6 unsaturated fatty acid that is precursor of arachidonic acid or dihomo-γ-linolenic acid among the fatty acids. As the omega 6 unsaturated fatty acids, there can be mentioned linoleic acid, γ-linolenic acid, dihomo-γ-linolenic acid, and the like, and as lipids containing said fatty acids as components there can be mentioned safflower oil, soybean oil, corn oil, cottonseed oil, Bio-γ(γ-linolenic acid-containing triglyceride), and the like.

The total amount of the substrate added is 0.001 to 10% by weight and preferably 0.5 to 10% by weight relative to the medium. These substrates may be added either before or immediately after inoculating the producer microorganism, or after the start of culturing, or they may be added at both time points. The addition after the start of culturing may be once, or more than once on an intermittent basis. Alternatively, they may be added continuously. These substrates may be added as the sole carbon source for culturing.

By culturing as described above, lipids containing arachidonic acid or dihomo-γ-linolenic acid can be formed and accumulated in large quantities in the cells. When liquid medium is used, arachidonic acid or dihomo-γ-linolenic acid can be harvested from the cultured cells as described below.

After culturing, cultured cells may be obtained from the culture by conventionally used means of separating a solid and a liquid such as centrifugation, filtration and the like. The cells are extensively washed with water, and preferably dried. Drying can be effected by lyophilization, air drying, and the like. Dried cells are preferably extracted with an organic solvent under a stream of nitrogen. As organic solvents, an ether, hexane, methanol, ethanol, chloroform, dichloromethane, petroleum ether, and the like can be used, and satisfactory results can also be obtained by alternate extraction with methanol and petroleum ether, or by extraction with a single layer solvent of chloroform-methanol-water. Evaporation of organic solvent from the extract under reduced pressure yields lipids containing arachidonic acid or dihomo-γ-linolenic acid.

Instead of the above-mentioned methods, wet cells may be used for extraction. In cases like this, solvents miscible with water such as methanol and ethanol, or mixed solvents miscible with water comprising these and water and/or other solvents may be used. The other procedures are similar to those described above.

In the lipids obtained as described above, various fatty acids are contained as components of lipid compounds, for example fat. They can be directly separated, but preferably they are separated as esters with a lower alcohol, such as γ-linolenic acid methyl, dihomo-γ-linolenic acid methyl, arachidonic acid methyl, and the like.

By converting into these esters, they can be readily separated from other lipid components, and can be readily separated from other fatty acids such as palmitic acid and oleic acid (these are also esterified at the same time as arachidonic acid or dihomo-γ-linolenic acid is esterified) that are formed in the culture. For example, in order to obtain a methyl ester of arachidonic acid or dihomo-γ-linolenic acid, the above extracted lipids are preferably treated with dry methanol-hydrochloric acid 5-10%, $BF_3$-methanol 10-15%, and the like at room temperature for 1-24 hours.

In order to recover arachidonic acid or dihomo-γ-linolenic acid from the above treated solution, extraction is preferably effected with such organic solvents as hexane, ether, ethyl acetate, and the like. The extract is then dried with anhydrous sodium sulfate and the organic solvents are preferably evaporated under reduced pressure to obtain a mixture predominantly composed of fatty acid esters. This mixture contains, in addition to the desired arachidonic acid or dihomo-γ-linolenic acid, fatty acid methyl esters such as palmitic acid methyl ester, stearic acid methyl ester, and oleic acid methyl ester. In order to isolate methyl ester of arachidonic acid or dihomo-γ-linolenic acid from mixtures of these fatty acid methyl esters, column chromatography, low temperature crystallization, urea inclusion, liquid-liquid countercurrent extraction can be used either singly or in combination.

In order to obtain arachidonic acid or dihomo-γ-linolenic acid from these methyl esters of arachidonic acid or dihomo-γ-linolenic acid, they are hydrolyzed in an alkali followed by extraction with an organic solvent such as ether and ethyl acetate.

Furthermore, in order to obtain arachidonic acid or dihomo-γ-linolenic acid without via methyl esters thereof, the above extract is decomposed with an alkali (e.g. 2 to 3 hours with 5% aqueous solution of sodium hydroxide), and then the decomposed material is subjected to extraction and purification according to the methods conventionally used for the extraction and purification of fatty acids.

The present invention will now be explained in more details with reference to specific examples.

EXAMPLES

Example 1

*Mortierella alpina* IFO8568 was inoculated into a large slant bottle containing 300 ml of Czapek agar medium (0.2% $NaNO_3$, 0.1% $K_2HPO_4$, 0.05% $MgSO_4.7H_2O$, 0.05% KCl, 0.001% $FeSO_4.7H_2O$, 3% sucrose, 2% agar, pH 6.0), and was cultured at 28° C. for 2 weeks. After culturing, 50 ml of sterile water to which had been added 2 drops of Tween80 was added to the large slant bottle, which was shaken sufficiently, and then filtered with 4 ply gauze. This procedure was repeated twice, and the filtrate was centrifuged at 8000×g for 10 minutes. Spores thus obtained were suspended into Tris/maleate buffer solution (pH 7.5) to $1 \times 10^6$/ml to prepare a spore solution.

To 1.0 ml of the spore solution thus obtained, 0.5 ml of 100 mM Tris/maleate buffer solution (pH 7.5) was added, and 500 µg of the NTG solution (N-methyl-N'-nitro-N-nitrosoguanidine 5 mg/deionized water 1 ml) was added, which was subjected to mutagenesis by incubating at 28° C. for 15 minutes. After adding 3 ml of 10% $Na_2S_2O_3$, the reaction mixture was centrifuged at 5500×g for 10 minutes, and the precipitate (spores subjected to mutagenesis) was washed with 3 ml of sterile water and centrifuged at 5500×g for 10 minutes, to which 2 ml of sterile water was added to prepare a NTG-treated spore suspension.

The NTG-treated spore suspension was diluted to about $10^{-3}$ to $10^{-4}$ and then plated on a GY agar plate (1% glucose, 0.5% yeast extract, 0.05% Triton X-100, 1.5% agar, pH 6.0). After incubating at 28° C., developed colonies were randomly picked up, and were cultured at 28° C. until growth can be seen, and after the growth was observed, the culture was stored.

The stored colonies that were picked up were cultured on a GY agar plate at 28° C. for 2 days and at 12° C. for 2 days, and then were punched out together with the agar prior to drying at 100° C. The dried cells obtained were placed into a screw capped test tube (16.5 mm Φ), to which 1 ml of methylene chloride and 2 ml of dry methanol-hydrochloric acid (10%) were added and were treated at 50° C. for 3 hours to methylesterify them. Four ml of n-hexane and 1 ml of water were added thereto, and extracted twice. After the solvent of the extract was evaporated using a centrifuge evaporator (40° C., 1 hour), the fatty acid methyl ester obtained was analyzed by capillary gas chromatography. After screening, *Mortierella alpina* SAM2153 (FERM P-15767) (FERM BP-6794) that does not produce eicosapentaenoic acid at a low temperature culture was obtained.

Example 2

To a GY agar plate (1% glucose, 0.5% yeast extract, 0.05% Triton X-100, 1.5% agar, pH 6.0), *Mortierella alpina* IFO8568 and *Mortierella alpina* SAM2153 (FERM P-15767) (FERM BP-6794) obtained in Example 1 were separately inoculated and were subjected to stationary culture. The culture temperature comprised the following 6 conditions:

1. 28° C. (2 days), 12° C. (2 days)
2. 28° C. (4 days)
3. 12° C. (6 days)
4. 28° C. (4 days), 12° C. (3 days)
5. 28° C. (7 days)
6. 12° C. (7 days)

After culturing, methyl esterification was conducted as in Example 1, and the fatty acid methyl ester thus obtained was analyzed by capillary gas chromatography. The results are shown in Table 1.

TABLE 1

Comparison of fatty acid composition of *Mortierella alpina* IFO8568 and SAM2153

| Culture condition (Days) | | Strain | Fatty acid composition (%) | | | | | | | | |
|---|---|---|---|---|---|---|---|---|---|---|---|
| 28° C. | 12° C. | | 16:0 | 18:0 | 18:1ω9 | 18:2ω6 | 18:3ω6 | DGLA | Ara | EPA | 24:0 | Others |
| 2 | 2 | IFO 8568 | 16.67 | 11.79 | 19.34 | 5.98 | 3.71 | 4.60 | 25.61 | 1.11 | 2.90 | 8.29 |
| 2 | 2 | SAM 2153 | 15.30 | 12.89 | 16.17 | 6.52 | 4.91 | 5.61 | 28.97 | 0 | 2.85 | 6.78 |
| 4 | 0 | IFO 8568 | 16.04 | 12.28 | 15.78 | 6.76 | 3.89 | 3.56 | 29.66 | 0 | 3.38 | 8.65 |
| 4 | 0 | SAM 2153 | 18.63 | 12.27 | 17.19 | 8.37 | 4.36 | 4.49 | 24.59 | 0 | 3.25 | 6.85 |
| 0 | 6 | IFO 8568 | 12.77 | 11.27 | 13.14 | 5.43 | 4.50 | 6.43 | 33.89 | 3.02 | 2.09 | 7.46 |
| 0 | 6 | SAM 2153 | 12.65 | 12.31 | 11.61 | 5.90 | 4.84 | 7.08 | 37.02 | 0 | 1.89 | 6.70 |
| 4 | 3 | IFO 8568 | 12.36 | 8.06 | 14.63 | 6.78 | 4.76 | 4.20 | 39.58 | 0 | 3.27 | 6.36 |
| 4 | 3 | SAM 2153 | 11.57 | 7.98 | 11.12 | 6.55 | 4.76 | 5.47 | 43.01 | 0 | 2.99 | 6.55 |
| 7 | 0 | IFO 8568 | 10.85 | 7.43 | 11.99 | 7.02 | 4.66 | 4.18 | 42.46 | 0 | 4.64 | 6.77 |
| 7 | 0 | SAM 2153 | 12.96 | 8.64 | 13.06 | 8.47 | 4.47 | 4.12 | 39.36 | 0 | 3.30 | 5.62 |
| 0 | 7 | IFO 8568 | 12.48 | 8.16 | 14.94 | 6.43 | 5.10 | 7.82 | 37.18 | 3.31 | 0.57 | 4.01 |
| 0 | 7 | SAM 2153 | 10.42 | 9.66 | 8.63 | 5.62 | 4.64 | 7.08 | 47.28 | 0 | 1.65 | 5.02 |

16:0, palmitic acid;
18:0, stearic acid;
18:1ω9, oleic acid;
18:2ω6, linoleic acid;
18:3ω6, γ-linolenic acid;
DGLA, dihomo-γ-linolenic acid;
Ara, arachidonic acid;
EPA, eicosapentaenoic acid;
24:0, tetracosanoic acid The parent strain IFO8568, when cultured at 12° C., produced eicosapentaenoic acid, and its ratio increased in proportion with the culturing time at 12° C., whereas the mutant strain *Mortierella alpina* SAM2153 (FERM P-15767) (FERM BP-6794) did not produce eicosapentaenoic acid at all even by culturing for a long time at 12° C., revealing that it is a mutant strain in which the activity of ω3 desaturase (enzymes that convert arachidonic acid to eicosapentaenoic acid) is lacking or extremely decreased. Also, since it was not capable of converting arachidonic acid to eicosapentaenoic acid, it was found that the content of arachidonic acid could be efficiently enhanced by culturing at a low temperature because arachidonic acid that otherwise would have been converted to eicosapentaenoic acid was accumulated by culturing at a low temperature.

Example 3

Two ml of a medium (pH 6.0) containing 4% glucose and 1% yeast extract was placed in a 10 ml Erlenmeyer flask and was sterilized at 120° C. for 20 minutes. One platinum loopful each of *Mortierella alpina* IFO8568 and *Mortierella alpina* SAM2153 (FERM P-15767) (FERM BP-6794) obtained in Example 1 were inoculated on the medium, and were cultured under shaking using a reciprocating shaker (150 rpm) at 12° C. for 7 days, or at 12° C. for 10 days. The results are shown in Table 2. It was confirmed in the liquid culture also that no eicosapentaenoic acid was produced, even by culturing at 12° C., resulting in an enhanced ratio and an increased amount of arachidonic acid produced.

TABLE 2

Comparison of fatty acid composition of and the amount of arachidonic acid produced by *Mortierella alpina* IFO8568 and SAM2153

| Culture condition | | | Degree of growth | Amount of Ara produced | Fatty acid composition (%) | | | | | | | | | |
|---|---|---|---|---|---|---|---|---|---|---|---|---|---|---|
| Temp. | Days | Strain | (g/l) | (g/l) | 16:0 | 18:0 | 18:1ω9 | 18:2ω6 | 18:3ω6 | DGLA | Ara | EPA | 24:0 | Others |
| 12° C. | 7 | IFO 8568 | 9.48 | 0.28 | 12.92 | 8.14 | 19.17 | 7.79 | 6.75 | 6.84 | 28.21 | 3.41 | 1.02 | 5.75 |
| | | SAM 2153 | 10.52 | 0.48 | 11.47 | 11.65 | 12.30 | 6.14 | 6.93 | 9.58 | 36.12 | 0 | 1.65 | 4.16 |
| 12° C. | 10 | IFO 8568 | 11.50 | 0.72 | 13.42 | 7.98 | 19.80 | 5.78 | 5.57 | 7.17 | 30.73 | 3.50 | 1.12 | 4.93 |
| | | SAM 2153 | 12.88 | 1.41 | 8.71 | 11.85 | 7.75 | 3.95 | 5.79 | 8.51 | 48.22 | 0 | 2.03 | 3.19 |

16:0, palmitic acid;
18:0, stearic acid;
18:1ω9, oleic acid;
18:2ω6, linoleic acid;
18:3ω6, γ-linolenic acid;
DGLA, dihomo-γ-linolenic acid;
Ara, arachidonic acid;
EPA, eicosapentaenoic acid;
24:0, tetracosanoic acid Example 4

To 2 ml of a medium (pH 6.0) containing 4% glucose and 1% yeast extract, substrates for arachidonic acid biosynthesis or lipids containing them shown in Table 3 were each added at 0.5%, and the mixture was placed in a 10 ml Erlenmeyer flask and was sterilized at 120° C. for 20 minutes. One platinum loopful of *Mortierella alpina* SAM2153 (FERM P-15767) (FERM BP-6794) obtained in Example 1 was inoculated on the medium, and was cultured under shaking using a reciprocating shaker (150 rpm) at 12° C. for 10 days. The results are shown in Table 3.

TABLE 3

| | Arachidonic acid | | |
|---|---|---|---|
| | Content | Amount produced | |
| Additive | (%) | (g/l) | (mg/g) |
| No addition | 48.22 | 1.41 | 109.2 |
| Octadecane | 49.23 | 1.46 | 111.2 |
| Sodium oleate | 50.10 | 1.56 | 119.3 |

TABLE 3-continued

| | Arachidonic acid | | |
|---|---|---|---|
| | Content | Amount produced | |
| Additive | (%) | (g/l) | (mg/g) |
| Sodium linoleate | 51.30 | 1.63 | 124.3 |
| Sodium linolenate | 52.71 | 1.65 | 123.5 |
| Methyl oleate | 52.92 | 1.68 | 127.1 |
| Methyl linoleate | 53.20 | 1.73 | 128.4 |
| Methyl linolenate | 53.25 | 1.74 | 128.6 |
| Soybean oil | 54.06 | 1.81 | 129.0 |
| Corn oil | 53.76 | 1.81 | 131.4 |
| Cottonseed oil | 54.88 | 1.84 | 130.9 |
| Safflower oil | 56.64 | 2.05 | 143.7 |

Example 5

Five liters of a medium (pH 6.0) containing 2% glucose, 1.5% soy flour protein, 0.3% $KH_2PO_4$, 0.05% $MgCl_2 \cdot 6H_2O$, 0.1% $Na_2SO_4$, and 0.1% soybean oil was placed in a 10 L jar fermentor and was sterilized at 120° C. for 30 minutes. *Mortierella alpina* SAM2153 (FERM P-15767) (FERM BP-6794) obtained in Example 1 was inoculated and was subjected to an airation and agitation culture at an aeration rate of 1 vvm for 10 days. The culture temperature was 20° C. at the start of culturing, and from day 3 it was gradually decreased to 12° C. Only on day 1, was 1% glucose added.

From day 2, 12 ml of the culture was sampled out, was methylesterified, and the fatty acid methyl esters obtained were analyzed by gas chromatography. FIGS. 1*a*, *b*, *c*, and *d* each show changes in the amount (g/l) of arachidonic acid produced, the ratio (%) of arachidonic acid to the total fatty acids, the degree of growth (g/l), and glucose concentrations (%) in the medium. Culturing at a low temperature in a 10 L jar fermentor was confirmed and surprisingly the ratio of arachidonic acid to the total fatty acids reached as high as 56.4% on day 10 of culturing. Analysis of lipid fractions in the intracellular lipids on day 10 of culturing revealed that triacylglycerol was 85.8%, free fatty acids 2.1%, diacylglycerol 0.5%, phosphatidyl ethanolamine 3.8%, phosphatidyl choline 3.9%, phosphatidyl serine 2.0%, and phosphatidic acid 1.9%.

Example 6

Five liters of a medium (pH 6.0) containing 2% glucose, 1.5% soy flour, 0.3% $KH_2PO_4$, 0.05% $MgCl_2.6H_2O$, 0.05% $CaCl_2.2H_2O$, 0.1% $Na_2SO_4$, and 0.1% soybean oil was placed in a 10 L jar fermentor and was sterilized at 120° C. for 30 minutes.

On the other hand, *Mortierella alpina* IFO8568 as a parent strain in a similar manner to Example 1, was subjected to mutation treatment again to obtain *Mortierella alpina* SAM2239, a strain in which ω3 desaturase activity was decreased.

This SAM2239 was inoculated and was subjected to an airation and agitation culture at an aeration rate of 1 vvm for 12 days. The culture temperature was 24° C. at the start of culturing, and from day 3 it was gradually decreased to 12° C. On day 1, 2, and 3, 1% glucose was added. On day 12, the final day of culturing, sampling was carried out, and the fatty acid methyl esters obtained were analyzed by gas chromatography. The results indicated that the ratio of arachidonic acid to the total fatty acids reached as high as 75.1% and the amount produced thereof was 4.1 g/l.

Reference to the microorganisms deposited under the Patent Cooperation Treaty, Rule 13-2, and the name of the Depository Authority Depository Authority:
  Name: the National Institute of Bioscience and Human Technology, Agency of Industrial Science and Technology
  Address: 1-3, Higashi 1-chome, Tsukuba city, Ibaraki pref., Japan Microorganism (1)
  Name: *Mortierella elongata* SAM2219.
  Accession number: FERM BP-1239
  Deposition Date: Mar. 19, 1986

Microorganism (2)
  Name: *Mortierella alpina* SAM2153
  Accession number: FERM BP-6794
  Deposition Date: Aug. 5, 1996

The invention claimed is:

1. A process for producing an arachidonic acid-containing microbial lipid comprising:
  culturing *Mortierella alpina* SAM2153 FERM BP-6794, at a temperature lower than the optimum growth temperature from the start of culturing or after culturing at the optimum growth temperature; and then
  recovering said arachidonic acid-containing microbial lipid from the culture.

2. The process according to claim 1 comprising culturing said *Mortierella alpina* SAM2153 FERM BP-6794, in a medium containing hydrocarbons, fatty acids, fatty acid esters, fatty acid salts, or lipids containing them as components; or adding to the culture in which said *Mortierella alpina* SAM2153 FERM BP-6794, is being cultured hydrocarbons, fatty acids, fatty acid esters, fatty acid salts, or lipids containing them as components, and then further culturing.

3. A process for producing an arachidonic acid-containing microbial lipid comprising:
  culturing *Mortierella alpina* SAM2153 FERM BP-6794, at a temperature lower than 20° C. from the start of culturing or after culturing at 20 to 40° C.; and then
  recovering said arachidonic acid-containing microbial lipid from the culture.

4. The method according to claim 3 comprising culturing said *Mortierella alpina* SAM2153 FERM BP-6794, in a medium containing hydrocarbons, fatty acids, fatty acid esters, fatty acid salts, or lipids containing them as components; or adding to the culture in which said *Mortierella alpina* SAM2153 FERM BP-6794, is being cultured hydrocarbons, fatty acids, fatty acid esters, fatty acid salts, or lipids containing them as components, and then further culturing.

* * * * *

UNITED STATES PATENT AND TRADEMARK OFFICE
CERTIFICATE OF CORRECTION

PATENT NO. : 7,585,651 B2  Page 1 of 1
APPLICATION NO. : 11/167224
DATED : September 8, 2009
INVENTOR(S) : Akimoto et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 455 days.

Signed and Sealed this

Fourteenth Day of December, 2010

David J. Kappos
*Director of the United States Patent and Trademark Office*